(12) United States Patent
Kenmochi et al.

(10) Patent No.: US 7,727,215 B2
(45) Date of Patent: Jun. 1, 2010

(54) WEARING ARTICLE

(75) Inventors: Yasuhiko Kenmochi, Kagawa-ken (JP); Akiyoshi Kinoshita, Kagawa-ken (JP); Natsuko Aoyagi, Kagawa-ken (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 11/773,399

(22) Filed: Jul. 3, 2007

(65) Prior Publication Data

US 2008/0021431 A1 Jan. 24, 2008

(30) Foreign Application Priority Data

Jul. 6, 2006 (JP) .............................. 2006-187147

(51) Int. Cl.
*A61F 13/15* (2006.01)
*A61F 13/20* (2006.01)

(52) U.S. Cl. ................................. 604/387; 604/385.01

(58) Field of Classification Search ............ 604/385.01, 604/385.03, 386–389
See application file for complete search history.

(56) References Cited

U.S. PATENT DOCUMENTS 5,370,634 A * 12/1994 Ando et al. ............ 604/385.21
6,905,488 B2 * 6/2005 Olson ........................ 604/389
2005/0080394 A1 4/2005 Otsubo et al.

FOREIGN PATENT DOCUMENTS

| JP | 28-3743 | 5/1953 |
| JP | 35-31347 | 11/1960 |
| JP | 2003-070833 | 3/2003 |

* cited by examiner

*Primary Examiner*—Michele Kidwell
(74) *Attorney, Agent, or Firm*—Brinks Hofer Gilson & Lione

(57) ABSTRACT

A wearing article includes a chassis and a fastening system. The chassis includes front and rear waist regions each having a waist hole defining edge and a waist hole elastic zone. The fastening system includes a first fastening component attached along side edge portions of one of the front and rear waist regions and having first and second ends in a longitudinal direction and a second fastening component attached along side edge portions of the other of the front and rear waist regions and detachably engageable with the first fastening component and first and second ends in the longitudinal direction. The first end of said second fastening component is beyond the first end of the first fastening component and an edge of the second waist hole elastic zone to a side of the second waist hole defining edge, with the first and second fastening components normally engaged with each other.

12 Claims, 3 Drawing Sheets

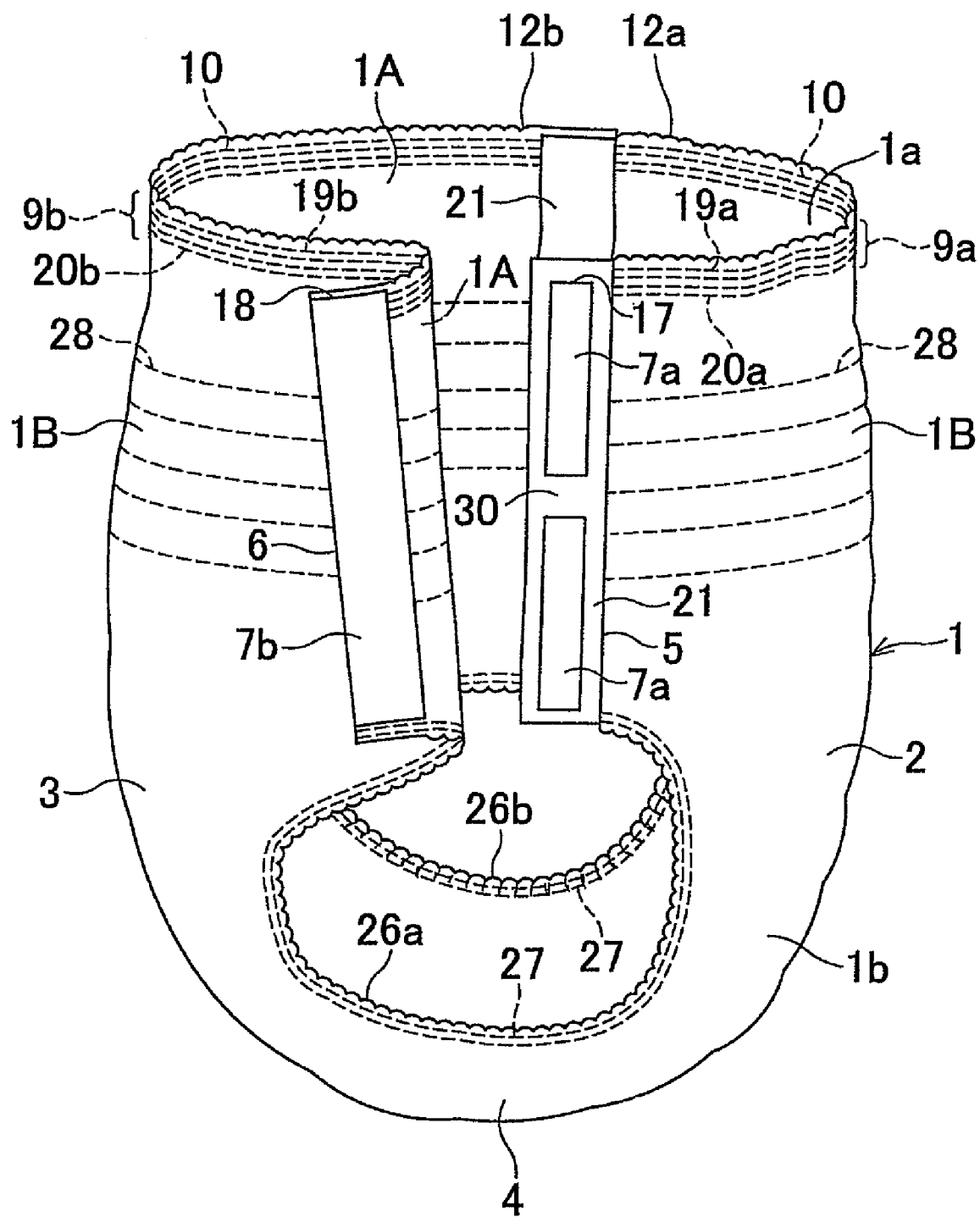

WEARING ARTICLE

BACKGROUND OF THE INVENTION

The present invention relates generally to a wearing article and more particularly to a diaper having transversely opposite side edges of front and rear waist regions adapted to be detachably fastened together.

There are disclosed absorbent garments such as, for example, disposable training pants with fasteners in side edges of front and rear waist regions in National Publication of patent application Based On Japanese Translated Version No. 2002-532147 (hereinafter referred to as "Reference").

The absorbent garment disclosed in Reference comprises side panels extending outward from an absorbent assembly in one of the front and rear waist regions in a transverse direction and mechanical fastening components provided in the other of the front and rear waist regions. The side panels define inner surfaces adapted to be refastenably fastened to the mechanical fastening components in order to retain the garment in a pants-like shape.

The absorbent garment disclosed in Reference is retained in the pants-like shape by refastenably fastening the one of the waist regions and the other of the waist regions to each other using the mechanical fastening components. However, the mechanical fastening components are attached to the side panels made of an elastomeric nonwoven fabric material and necessarily result in undesirable situation. Specifically, there are anxieties that the elastomeric nonwoven fabric material may curl up in vicinities of respective upper edges of the waist regions during use of the absorbent garment as the side panels made of the elastomeric nonwoven fabric material contracts in a waist surrounding direction, leading to deterioration of appearance and fit and even to peeling off of the fastening components. Particularly when hook elements constituting the mechanical fastening components are peeled off, the hook elements may irritate the wearer's skin, causing the wearer to experience a feeling of discomfort and/or causing garments and bedclothes to be damaged.

SUMMARY OF THE INVENTION

In view of the problem as has been described above, it is an object of the present invention to provide a wearing article having fastening components adapted to be refastenably fastened to each other improved so that phenomenon of curl up possibly occurring in transversely opposite side edge portions of the article due to contraction of elastic elements provided along waist hole defining edges can be effectively constrained.

According to the present invention, there is provided a wearing article comprising: a chassis comprising a longitudinal direction, a transverse direction and a waist surrounding direction; a body side surface and a garment side surface; a first waist region corresponding to one of front and rear waist region and having a first waist hole defining edge, a second waist region corresponding to the other of said front and rear waist regions and having a second waist hole defining edge and a crotch region between the first and second waist regions; first and second waist hole elastic zones respectively extending along the first and second waist hole defining edges, with the first and second waist regions folded in two along an imaginary transverse center line of the crotch region so that the front and rear waist regions are opposed to each other; and a fastening system for connecting transversely opposite side edge portions of the first and second waist regions to each other. The first and second waist hole elastic zones respectively have first edge adjacent to the first waist hole defining edge and second edges opposite to the first edge. The fastening system comprises a first fastening component which elongates in the longitudinal direction and has a first end adjacent to the first waist hole defining edge and a second end adjacent to the crotch region, and a second fastening component which elongates in the longitudinal direction and has a first end adjacent to the second waist hole defining edge and a second end adjacent to the crotch region and is detachably engageable with the first fastening component.

The present invention further comprises the first end of said second fastening component being beyond the first end of said first fastening component and the first edge of the second waist hole elastic zone to a side of the second waist hole defining edge, with the transversely opposite side edge potions of the first and second waist regions respectively connected by the first and second fastening components engaged with each other so that at least the first edges of the first edge and the second edges of the first and second waist hole elastic zones are aligned in a straight line in the waist surrounding direction.

The present invention may include the following preferred embodiments.

An embodiment wherein the first end of the fastening component is beyond the first edge of the first waist hole elastic zone to a side of the waist hole defining edge.

An embodiment wherein the first edge of the first waist hole elastic zone is positioned on or beyond the first end of the first fastening component to the side of the first waist hole defining edge.

An embodiment wherein the first edge of said first waist hole elastic zone and the first end of the first fastening component is spaced apart from each other by a distance in a range of 0 to 30 mm.

An embodiment wherein the second end of the first waist hole elastic zone is spaced apart from the first end of the first fastening component toward a side of the crotch region.

An embodiment wherein dimensions of the second fastening component in the longitudinal and transverse directions are greater than those of the first fastening component.

An embodiment wherein the first fastening component is divided in the longitudinal direction into two or more while the divided first components are spaced apart from each other in the longitudinal direction.

An embodiment wherein the first fastening component comprises a hook element and the second fastening component comprises a loop element.

An embodiment wherein the hook element is attached on the garment side surface.

An embodiment wherein the first fastening component is attached to the transversely opposite side edge portions of the first waist region in substantially full length of each of the transversely opposite side edge portions of the first waist region with interposition of a reinforcing side sheet.

An embodiment wherein the first and second elastic zones extend in substantially full length of each of the first and second waist regions in the transverse direction or the waist surrounding direction wherein portions of the first and second waist hole elastic zones in which the first and second fastening components are intersected with the first and second waist hole elastic zones in said transversely opposite side edge portions, are substantially non-elasticized.

An embodiment wherein the chassis comprises a liquid-pervious body side liner defining the body side surface, a liquid-impervious outer cover defining the garment side surface and a liquid-absorbent core disposed between the body side liner and the outer cover.

According to the present invention, the first end of the second fastening component is beyond the first edge of the second waist hole elastic zone to the side of the second waist hole defining edge, so that a zone of the second waist hole defining edge in a vicinity of the side edge portion of the second waist region provided with the second fastening component is free from any significant influence of a contractile force of the second waist hole elastic zone. In this way, the zone of the second waist hole defining edge in the vicinity of the side edge portion of the second waist region are reliably prevented from curling up.

According to the embodiment wherein the first end of the first fastening component is beyond the first edge of the first waist hole elastic zone to the side of the first waist hole defining edge, the first fastening component has a relatively high stiffness serving to put a restraint on deformation possibly occurring in a zone of the side edge portion of the first waist region provided with the first fastening component as well as in the vicinity thereof. Consequentially, the side edge portion as well as the vicinity of the waist hole defining edge are reliably prevented from curling up due to the contractile force of the first waist hole elastic zone.

According to the embodiments wherein the first edge of the first waist hole elastic zone is positioned on or beyond the first end of the first fastening component to the side of the first waist hole defining edge, and the spaced-apart distance between the first edge of the first waist hole elastic zone and the first end of the first fastening component is in a range of 0 to 30 mm, the first fastening component having a relatively high stiffness serves to put a restraint on deformation possibly occurring in the zone of the side edge portion of the first waist region provided with the first fastening component as well as in the vicinity of the side edge portion and thereby to prevent the first waist hole defining edge in the vicinity of the side edges of the first waist region curling up.

According to the embodiment wherein the dimensions of the second fastening component in the longitudinal and transverse directions are greater than those of the first fastening component, it is easy for the wearer to engage the first and second fastening component with each other so that these fastening components may be engaged with each other without being out of place to each other in the longitudinal and/or transverse directions.

According to the embodiment wherein the first fastening component is divided in the longitudinal direction into two or more while the divided first fastening components are spaced apart from each other in the longitudinal direction, the wearer's fingers may be easily inserted into a gap created between the divided first fastening components to disengage the divided first fastening components and the second fastening component from each other.

According to the embodiment wherein the first fastening component is attached to the transversely opposite side edge portion of the first waist region with interposition of the reinforcing side sheet, zones of the first waist hole defining edge in vicinities of the first fastening component and the side edge portion of the first waist region are reliably prevented from being deformable.

According to the embodiment wherein the portions of the first and second waist hole elastic zones in which the first and second fastening components are intersected with the first and second waist hole elastic zones are substantially non-elasticized, the first and second fastening components are reliably prevented the zones from being deformable due to influence of the contractile force of the first and second elastic zones.

BRIEF DESCRIPTION OF THE DRAWINGS

FIG. 3 is a perspective view of the diaper according to an alternative embodiment of the present invention.

DETAILED DESCRIPTION OF THE PREFERRED EMBODIMENTS

Details of a wearing article according to the present invention will be more fully understood from the description of a disposable diaper as a typical embodiment given hereunder with reference to the accompanying drawings.

Figure 1:
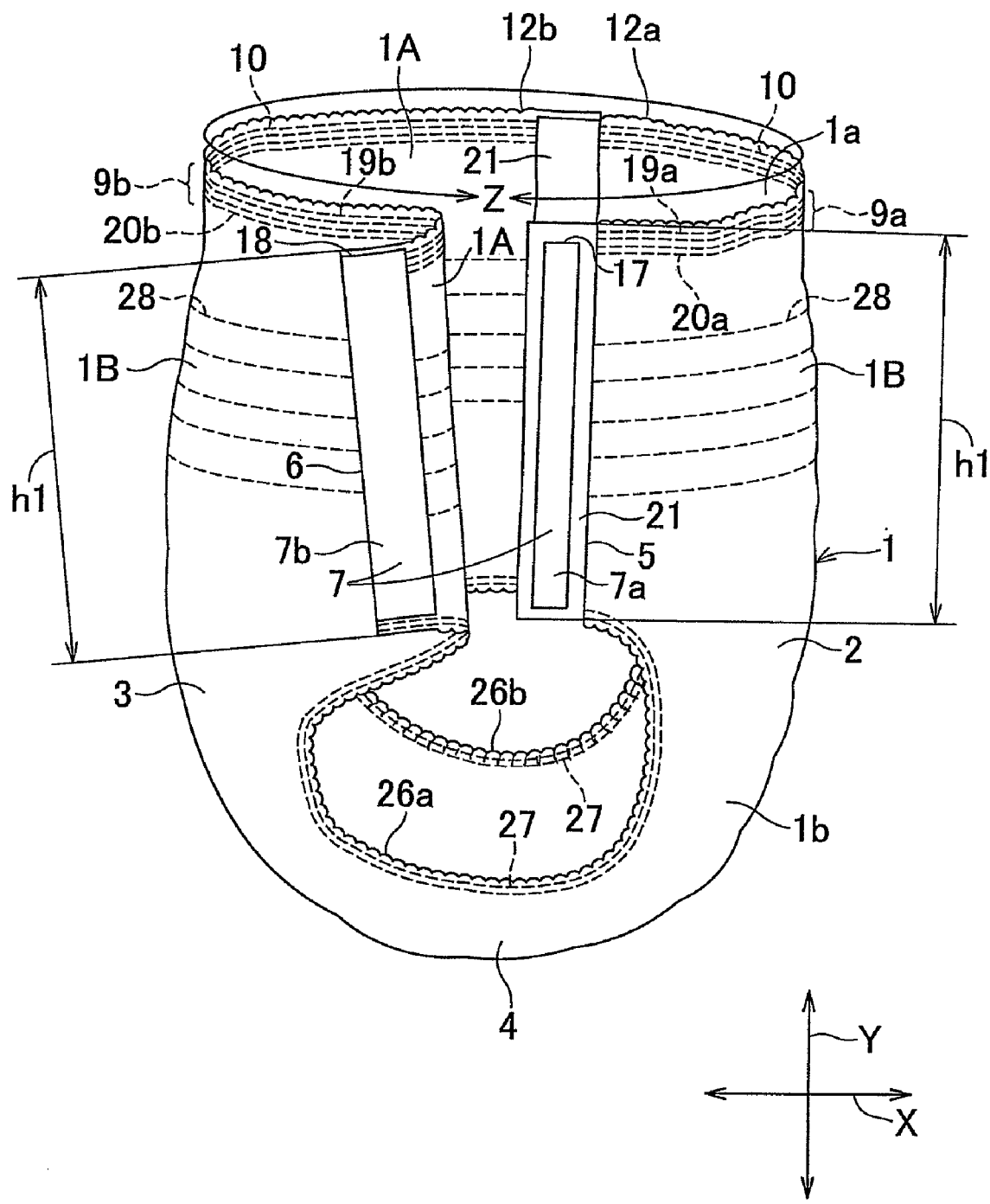
FIG. 1 is a perspective view of a diaper in which one side edge portion of opposite side edge portions of front and rear waist regions are disconnected.

In FIG. 1, a disposable diaper is shown in a perspective view in a state where the diaper is folded in two along an imaginary transverse center line in a crotch region 4 so that front and rear waist region 2, 3 are opposed to each other and has one side edge portion of the front and rear waist regions 2, 3 connected with each other and the other side edge portion disconnected with each other. The diaper comprises an absorbent chassis 1 and a fastening system 7. The absorbent chassis 1 has a longitudinal direction Y, a transverse direction X and a waist surrounding direction Z; the absorbent chassis 1 comprises a body side surface 1a and a garment side surface 1b; a front waist region 2, rear waist region 3, and crotch region 4 extending between these regions which are longitudinally arranged; a liquid-pervious body side liner 1A defining the body side surface 1a, a liquid-impervious outer cover 1B defining the garment side surface 1b and a liquid-absorbent core (not shown) disposed between the liner and the outer cover. However, the liquid-absorbent core is not essential in some articles to which the present invention is applied. Dimension hi of transversely opposite side edge portions 5, 6 of the front and rear waist regions 2, 3 as measured in the longitudinal direction Y are substantially equal.

The fastening system 7 comprises a hook element 7a which is a first fastening component as a mechanical fastening component and a loop element 7b which is a second fastening component as a mechanical fastening component to engage with the hook element 7a detachably. The hook element 7a has a plurality of hooks, elongates in the longitudinal direction Y and is attached to the front waist region 2 along the transversely opposite side edge portions 5 (hereinafter only one side of the transversely opposite side edge portions 5 is described) with interposition of a reinforcing side sheet 21 attached to the garment side surface 1b. The loop element 7b has a plurality of loops, elongates in the longitudinal direction Y and is attached to the rear waist region 3 along the transversely opposite side edge portions 6 (hereinafter only one side of the transversely opposite side edge portions 6 is described). The reinforcing side sheet 21 elongates in the longitudinal direction Y and is attached to the front waist region 2 along the side edge portion 5 in substantially full length of the side edge portion 5. The hook element 7a has a dimension as measured in the longitudinal direction Y slightly smaller than a dimension h1 of the front waist region 2 as measured in the longitudinal direction Y or a dimension of the reinforcing side sheet 21 as measured in the longitudinal direction Y, and a dimension as measured in the transverse direction X slightly smaller than the dimension of the reinforcing side sheet 21 as measured in the transverse direction X. In other words, a periphery of the hook element 7a is inside and spaced apart from a periphery of the reinforcing side sheet 21. The absorbent chassis 1 is retained in a pants-like shape as shown in FIG. 1 when the hook element 7a of the front waist region 2 and the loop element 7b of the rear waist region 3 are engaged with each other.

The absorbent chassis 1 further comprises front and rear waist hole elastic zones 9a, 9b extending along the front and rear waist hole defining edges 12a, 12b in the transverse direction X of the front and rear waist regions 2, 3 and a pair of leg hole elastic zones 26a, 26b extending along a pair of leg hole defining edges in the crotch region 4. A dimension between an upper edge 19a of the front waist hole elastic zone 9a and a dimension between an upper edge 19b of the rear waist hole elastic zone 9b and a lower edge 20b of the rear waist hole elastic zone 9b are substantially constant in full length of the respective front and rear waist hole elastic zones 9a, 9b and they are the same. However, the dimensions of the front and rear elastic zones 9a, 9b may be different from each other. In this case, at least the upper edges 19a, 19b of the front and rear waist hole elastic zones 9a, 9b are preferably aligned in a substantially straight line along the waist surrounding direction Z, in other words, they are positioned substantially at the same height (level) in FIG. 1 when the transversely opposite side edge portions 5, 6 of the front and rear waist regions 2, 3 are normally connected to each other by means of the hook element 7a and the loop element 7b. The front and rear waist hole elastic zones 9a, 9b and the leg hole elastic zones 26a, 26b are defined by attaching of a plurality of rubber strings 10, 27 in a stretched state by means of hot melt adhesive (not shown) to the absorbent chassis 1 in which the rubber strings 10, 27 are sandwiched between the body side liner 1A and the outer cover 1B. Under contractile force of these rubber strings 10, 27, the front and rear waist hole elastic zones 9a, 9b and the leg hole elastic zones 26a, 26b contract to provide a desired fit around the wearer's waist and legs and to prevent the diaper from slipping down the wearer's waist. At the same time, the contractile force of the rubber strings 10 of the front and rear waist hole elastic zones 9a, 9b is exerted on the opposite side edges 5, 6 of the front and rear waist regions 2, 3, respectively, in the vicinity of the respective front and rear waist hole defining edges 12a, 12b so as to potentially draw them apart. In addition, the chassis 1 comprises a plurality of auxiliary elastic elements 28 which are contractible in the waist surrounding direction and attached in a stretched state so as to be sandwiched between the body side liner 1A and the outer cover 1B by means of hot melt adhesive (not shown). Generally a stretching force of rubber strings as the auxiliary elastic elements 28 are weaker than those of the rubber strings as the front and rear waist hole elastic zones 9a, 9b.

The hook element 7a may be made, for example, of thermoplastic resin such as polypropylene or polyethylene. The hook element 7a exemplarily comprise a plurality of hooks rising from a base sheet, wherein a height of the hook is in a range of 200 to 400 μm and the number of the hooks is in a range of 600 to 2500/(25.4×25.4 mm). The hook element 7a generally has a stiffness substantially equal to or higher than that of the loop element 7b.

The loop element 7b may be formed, for example, by bonding nylon fibers having piles from 10 to 50/cm$^2$ to a polypropylene film so that this assembly may have a total basis weight of 30 to 50 g/m$^2$. Alternatively, the loop element 7b may be replaced by an appropriate fibrous nonwoven fabric adapted to be engaged with the hook element 7a. In this case, a stiffness of the loop element 7b is much lower than that of the hook element 7a.

Both the hook element 7a and the loop element 7b are put in positions so that respective upper ends 17, 18 thereof are spaced apart from the respective front and rear waist hole defining edges 12a, 12b of the front and rear waist regions 2, 3 toward the crotch region 4 in order to prevent those upper ends 17, 18 protruding outwardly in the longitrudinal direction Y beyond the front and rear waist hole defining edges 12a, 12b. Such placement of the upper end 17 of the hook element 7a and the upper end 18 of the loop element 7b spaced apart from the respective upper edges 12a, 12b of the front and rear waist regions 2, 3 makes it possible to establish a positional tolerance, for example, of the hook element 7a in the course of production on the basis of a process capability, on one hand, to avoid, for example, an anxiety that the wearer might experience a feeling of discomfort due to an exposed portion of the hook element 7a and the loop element 7b, especially the hook element 7a, on the other hand.

The body side liner 1A may typically be a nonwoven fabric, a perforated film made of thermoplastic polymer, while the outer cover 1B may typically be a film or nonwoven fabric made of thermoplastic polymer, or a composite sheet consisting of these film and nonwoven fabric layered with each other. The reinforcing side sheet 21 may typically be a nonwoven fabric, or a perforated film made of thermoplastic polymer. Attachment of the hook element 7a and the loop element 7b may be carried out by means of well known art such as hot melt adhesive or heat sealing technique. The respective portions of the rubber strings 10 for the waist hole elastic zones 9a, 9b as well as the rubber strings for the auxiliary elastic elements 28 intersecting with the hook element 7a and the loop element 7b, respectively are preferably subjected to an appropriate treatment to inactivate the elasticity. The treatment includes cutting, covering with a hot melt adhesive and chemical treatment. Such treatment makes it possible to prevent the hook element 7a and the loop elements 7b from getting wrinkles potentially interfering with engagement of them.

Figure 2A:
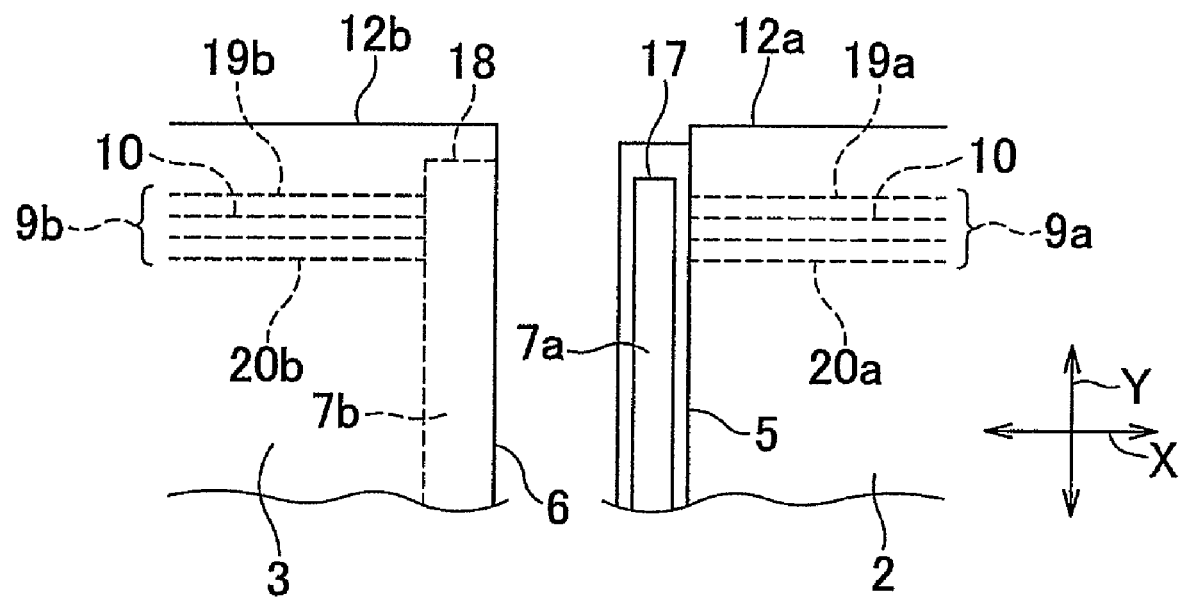
FIG. 2A is a diagram schematically illustrating the case in which an upper end of a first fastening component (hook element) is positioned at a level higher than an upper edge of a waist hole elastic zone and FIG. 2B is a diagram schematically illustrating the case in which an upper end of a first fastening component (hook element) is positioned at a level lower than an upper edge of a waist hole elastic zone.
Figure 2B:
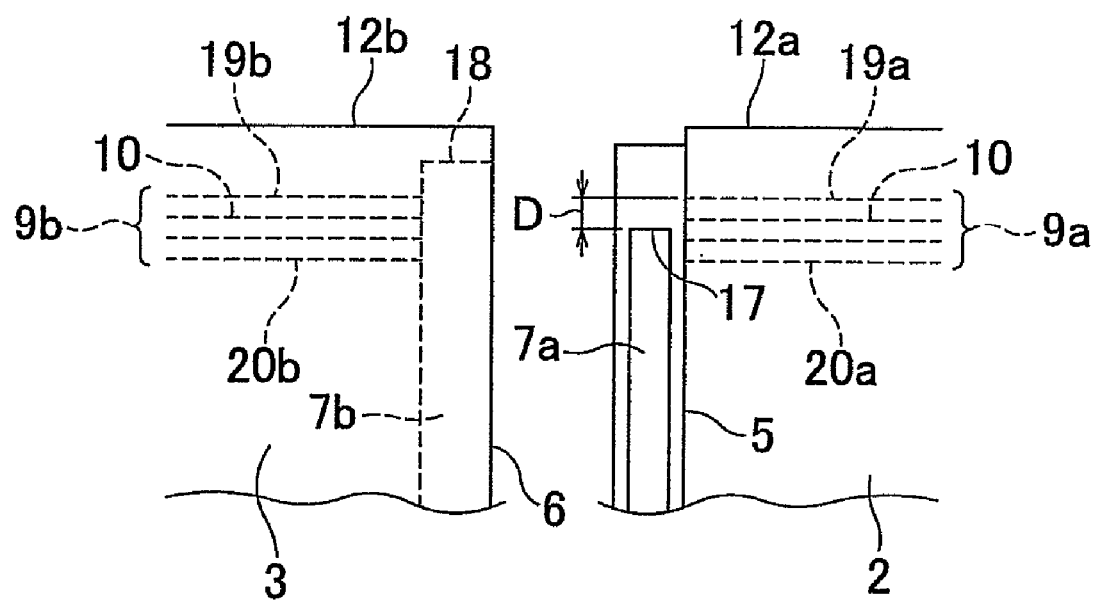

FIG. 2A is a schematic diagram illustrating the case in which the upper end 17 of the hook element 7a is beyond the upper edge 19a of the front waist hole elastic zone 9a to a side of the front waist hole defining edge 12a (and also to a side of the rear waist hole defining edge 12b), in other words, at the level above the upper edge 19a of the front waist hole elastic zone 9a in a sate where the front an rear waist hole defining edges 12a, 12b of the front and rear waist regions 2, 3 are aligned in a substantially straight line in the waist surrounding direction Z, in other words, they are positioned substantially at the same height (level) while the front and rear waist hole elastic zones 9a, 9b are aligned in a substantially straight line in the waist surrounding direction Z, in other words, they are positioned substantially at the same height (level). FIG. 2B is a schematic diagram illustrating the case in which the upper end 17 of the hook element 7a is beyond (below) the upper edge 19a of the front waist hole elastic zone 9a to a side of the crotch region 4, to be exact, the upper end 17 is between the upper edge 19 and the lower edge 20a in a sate where the front an rear waist hole defining edges 12a, 12b of the front and rear waist regions 2, 3 are aligned in a substantially straight line in the waist surrounding direction Z, in other words, they are positioned substantially at the same height (level) while the front and rear waist hole elastic zones 9a, 9b are aligned in a substantially straight line in the waist surrounding direction Z, in other words, they are positioned substantially at the same height (level). In each case, the upper end 18 of the loop element 7b is positioned at the level beyond both the upper end 17 of the hook element 7a and the upper end 19b of the rear waist hole elastic zone 9b, in other words, the upper end 18 is positioned at the level above the upper edge 19b of the rear waist hole elastic zone 9b.

The placement of the upper end 18 of the loop element 7b above the rear waist hole elastic zone 9b advantageously ensures that the side edge portion 6 in the vicinity of the rear waist hole elastic zone 9b is free from influence of the contractile force of the rubber strings 10 for the rear waist hole elastic zone 9b in a state where the transversely opposite side edge portions 5, 6 of the front and rear waist regions 2, 3 are normally connected to each other by means of the hook element 7a and the loop element 7b (refer to FIG. 1) so that the front an rear waist hole defining edges 12a, 12b of the front and rear waist regions 2, 3 are aligned in a substantially straight line in the waist surrounding direction Z while the front and rear waist hole elastic zones 9a, 9b are aligned in a substantially straight line in the waist surrounding direction Z. Consequentially, such portion is prevented from curling up due to deformation. In addition, the side edge portion 6 in the vicinity of the rear waist hole elastic zone 9b is kept in a sufficiently flattened state to be easily held by the hands when the wearer connects the front and rear waist regions 2, 3 to each other. In this way, convenience for handling the diaper is improved.

In the case of the arrangement such that upper end 17 of the hook element 7a is positioned above the upper edge 19 of the front waist hole elastic zone 9a as illustrated in FIG. 2A, the hook element 7a having a stiffness relatively higher than that of the front waist region 2 serves to constrain deformation of front waist region 2 in the vicinity of the side edge portion 5 and the side edge portion 5 of the front waist region 2 as well as the upper edge 19a is free from the contractile force of the waist hole elastic zone 9a. Consequentially the side edge portion 5 in the vicinity of the waist hole defining edge 12a is prevented from becoming deformed and eventually curling up.

In the FIG. 2B, the upper edge 19a of the front waist hole elastic zone 9a is beyond the upper end 17 of the hook element 7a to a side of the front waist hole defining edge 12a, in other words, the upper edge 19a is positioned above the upper end 17 a distance D by which the upper edge 19a of the front waist hole elastic zone 9a is spaced apart from the upper end 17 of the hook element 7a is 30 mm or less. Accordingly, the upper edge 19a of the waist hole elastic zone 9a and the upper end 17 of the hook element 7a may substantially overlap, though it is not shown in Figures. A lower end 20a of the front waist hole elastic zone 9a is below the upper end 17 of the hook element 7a (on the side of the crotch region 4).

In this manner, the distance D by which the upper edge 19a of the front waist hole elastic zone 9a is spaced apart from the upper end 17 of the hook element 7a may be selected within a range of 0 to 30 mm to ensure that the hook element 7a having a stiffness relatively higher than that of the front waist region 2 serves to constrain any significant deformation possibly occurring in the side edge portion 5 in the vicinity of the front waist hole defining edge 12a. Therefore, it is not likely that the side edge portion 5 in the vicinity of the front waist hole defining edge 12a might be deformed and eventually curl up. If the distance D exceeds 30 mm, the effect provided by the hook element 7a to constrain undesirable deformation possibly occurring in the side edge portion 5 in the vicinity of the front waist hole defining edge 12a will decrease and it will lead to curling up.

The lower edge 20a of the front waist hole elastic zone 9a is preferably positioned at a level lower than the upper end 17 of the hook element 7a. With such arrangement, the reinforcing side sheet 21 extending between the lower edge 20a of the front waist hole elastic zone 9a and the upper end 17 of the hook element 7a is protected against deformation and curling up due to the contractile force of the front waist hole elastic zone 9a.

FIG. 3 is a perspective view showing another preferred embodiment of the present invention. In the case of this embodiment, each of the hook elements 7a is divided in the longitudinal direction Y into two and attached to the reinforcing side sheet 21 so as to be spaced apart from each other in the longitudinal direction Y. The remaining arrangement is the same as in the case of the diaper shown in FIG. 1 and will not described here repetitively. According to this embodiment, a zone 30 extending between two hook elements 7a has a stiffness lower than the zones carrying the respective hook elements 7a thereon and left out of engagement with the loop element 7b. Under the contractile force of the auxiliary elastic elements 28, the zone 30 is deformed to create a gap between the paired hook element 7a and the loop element 7b. When it is desired to put off the used diaper, the wearer can easily disengage the hook element 7a from the loop element 7b by inserting the finger into these gaps created in the zones 30.

A distance between the divided hook elements 7a is preferably selected within a range of 10 to 40 mm. The distance less than 10 mm will make it difficult to insert the wearer's finger into the gap. The distance exceeding 40 mm, on the contrary, will unacceptably reduce the area of the individual hook element 7a and make it impossible to assure adequate firm engagement with the loop element 7b.

While the specific embodiments have been described above, the foregoing is illustrative of the present invention and is not to be construed as limiting thereof. Those skilled in the art readily appreciate that many modifications are possible in these embodiments without materially departing from the scope of the invention. For example, it is possible to attach the hook element 7a directly to the outer cover 1B in the front waist region 2 without interposition of the reinforcing side sheet 21. It is also possible to use a pressure-sensitive adhesive tape fastener by substituting a pressure-sensitive adhesive tape material for the hook element 7a and by substituting a sheet attachable to the adhesive tape material for the loop element 7b. In some cases, both the first and second fastening component constituting the mechanical fastener or the pressure-sensitive adhesive tape fastener may be divided in the longitudinal direction Y and/or the transverse direction X into two or more. Furthermore, it is also contemplated to provide the front and rear waist hole elastic zones 9a, 9b in the form of elasticized nonwoven fabric or relatively wide rubber band. Unlike the embodiment shown in Figures, it is also possible to attach the first fastening component to the side edge portion 6 in the rear waist region 3 and to the second fastening component to the side edge portion 5 of the front waist region 2.

The arrangement that the hook element 7a is attached to the garment side surface 1b so as to face away from the wearer's body may be replaced by the arrangement that the hook element 7a is attached to the body side surface 1a so as to face the wearer's body. The arrangement that the hook element 7a faces away from the wearer's body is effective to prevent the wearer from experience a feeling of discomfort. The arrangement that the hook element 7a faces the wearer's body is effective to protect garments and/or bedclothes from being damaged by the hook element 7a. While the alternative arrangement that the hook element 7a is divided into two has been illustrated and described, it is possible to divide the hook element 7a into three or more.

The present invention is applicable to training pants, diapers for incontinent patients, diaper covers (holders) or the like, other than the disposable diapers described above.

The entire discloses of Japanese Patent application No. 2006-187147 filed on Jul. 6, 2006 including specification, drawings and abstract are herein incorporated by reference in its entirety.

What is claimed is:

1. A wearing article comprising:
a chassis comprising
a longitudinal direction, a transverse direction and a waist surrounding direction;
a body side surface and a garment side surface;
a first waist region corresponding to one of front and rear waist regions and having a first waist hole defining edge, a second waist region corresponding to the other of said front and rear waist regions and having a second waist hole defining edge and a crotch region between said first and second waist regions;
first and second waist hole elastic zones respectively extending along said first and second waist hole defining edges, with said first and second waist regions folded in two along an imaginary transverse center line of said crotch region so that said first and second waist regions are opposed to each other;
a fastening system for connecting transversely opposite side edge portions of said first and second waist regions to each other;
said first and second waist hole elastic zones respectively having a first edge adjacent to said first waist hole defining edge and a second edge opposite to said first edge;
said fastening system comprising a first fastening component which elongates in said longitudinal direction and has a first end adjacent to said first waist hole defining edge and a second end adjacent to said crotch region, and a second fastening component which elongates in said longitudinal direction and has a first end adjacent to said second waist hole defining edge and a second end adjacent to said crotch region and is detachably engageable with said first fastening component; and
said first end of said second fastening component being positioned longitudinally beyond said first end of said first fastening component and also positioned longitudinally outward beyond said first edge of said second waist hole elastic zone to a side of said second waist hole defining edge, with said transversely opposite side portions of said first and second waist regions respectively connected by said first and second fastening components being engaged with each other so that at least said first edges of said first and second waist hole elastic zones are aligned in a straight line in said waist surrounding direction.

2. The article according to claim 1, wherein said first end of said first fastening component is beyond said first edge of said first waist hole elastic zone to a side of said first waist hole defining edge.

3. The article according to claim 1, wherein said first edge of said first waist hole elastic zone is positioned on or beyond said first end of said first fastening component to the side of said first waist hole defining edge.

4. The article according to claim 3, wherein said first edge of said first waist hole elastic zone and said first end of said first fastening component is spaced apart from each other by a distance in a range of 0 to 30 mm.

5. The article according to claim 3, wherein said second end of said first waist hole elastic zone is spaced apart from said first end of said first fastening component toward a side of said crotch region.

6. The article according to claim 1, wherein dimensions of said second fastening component in said longitudinal and transverse directions are greater than those of said first fastening component.

7. The article according to claim 1, wherein said first fastening component is divided in said longitudinal direction into two or more while the divided first fastening components are spaced apart from each other in said longitudinal direction.

8. The article according to claim 1, wherein said first fastening component comprises a hook element and said second fastening component comprises a loop element.

9. The article according to claim 8, wherein said hook element is attached on said garment side surface.

10. The article according to claim 1, wherein said first fastening component is attached to said transversely opposite side edge portions of said first waist region in substantially full length of each of said transversely opposite side edge portions of said first waist region with interposition of a reinforcing side sheet.

11. The article according to claim 1, wherein said first and second waist hole elastic zones extend in substantially full length of each of said first and second waist regions in said transverse direction or said waist surrounding direction wherein portions of said first and second waist hole elastic zones in which said first and second fastening components are intersected with said first and second waist hole elastic zones in said transversely opposite side edge portions, are substantially non-elasticized.

12. The article according to claim 1, wherein said chassis comprises a liquid-pervious body side liner defining said body side surface, a liquid-impervious outer cover defining said garment side surface and a liquid-absorbent core disposed between said body side liner and said outer cover.

* * * * *